(12) United States Patent
Kim et al.

(10) Patent No.: US 8,435,748 B2
(45) Date of Patent: May 7, 2013

(54) METHOD FOR MONITORING, DIAGNOSING, AND SCREENING CANCER THROUGH MEASURING THE CONCENTRATION OF DES-R PROTHROMBIN ACTIVATION PEPTIDE FRAGMENT F2 (DES-R F2) IN A SERUM

(75) Inventors: Chul Woo Kim, Guri-si (KR); Pil Je Park, Seoul (KR); Yong-Sung Shin, Seoul (KR); Kil Hyon Lee, Seoul (KR); Ho Sang Shin, Seoul (KR); Byoung-Kwon Kim, Seoul (KR)

(73) Assignee: Bioinfra Inc., Seoul (KR)

( * ) Notice: Subject to any disclaimer, the term of this patent is extended or adjusted under 35 U.S.C. 154(b) by 203 days.

(21) Appl. No.: 12/993,198

(22) PCT Filed: Mar. 13, 2009

(86) PCT No.: PCT/KR2009/001266
§ 371 (c)(1),
(2), (4) Date: Nov. 17, 2010

(87) PCT Pub. No.: WO2009/113832
PCT Pub. Date: Sep. 17, 2009

(65) Prior Publication Data
US 2011/0086404 A1      Apr. 14, 2011

(30) Foreign Application Priority Data
Mar. 14, 2008   (KR) .......................... 10-2008-0023803

(51) Int. Cl.
*G01N 33/53*       (2006.01)
(52) U.S. Cl.
USPC ......................................................... 435/7.1

(58) Field of Classification Search .................. None
See application file for complete search history.

(56) References Cited

U.S. PATENT DOCUMENTS 5,830,681 A *  11/1998  Hursting et al. ............. 435/7.94
6,541,275 B1    4/2003  Ruiz et al.

FOREIGN PATENT DOCUMENTS

WO        WO 00/14209       *   3/2000

OTHER PUBLICATIONS

Gieseler, F., et al. "Activated coagulation factors in human malignant effusions and their contribution to cancer cell metastasis and therapy," Thrombosis and Haemostasis, vol. 97(6), pp. 1023-1030 (Jun. 2007).

Lind, S.E., et al. "Correlates of thrombin generation in patients with advanced prostate cancer," Thrombosis and Haemostasis, vol. 89(1), pp. 185-189 (Jan. 2003).

Wojtukiewicz M.Z., et al. Expression of prothrombin fragment 1+2 in cancer tissue as an indicator of local activation of blood coagulation. Thrombosis Research, vol. 97(5), pp. 335-342 (Mar. 2000).

* cited by examiner

*Primary Examiner* — Sean Aeder
(74) *Attorney, Agent, or Firm* — Lucas & Mercanti, LLP

(57) ABSTRACT

The present invention relates to a method for diagnosis and screening of cancer by measuring the expression of des-R prothrombin activation peptide fragment F2 (des-R F2) in serum, more precisely, des-R-prothrombin activation peptide fragment F2 which is the protein marker down-regulated specifically in liver cancer, breast cancer, and stomach cancer, and a method for diagnosis and screening of liver cancer, breast cancer, and stomach cancer by quantifying the protein marker. The protein marker of the present invention can be effectively used for diagnosis and screening of liver cancer, breast cancer and stomach cancer by comparing the expression of the said protein marker in a normal subject with that of a liver cancer, breast cancer, or stomach cancer patients.

14 Claims, 11 Drawing Sheets

Fig. 9

| Start-End | Observed | Mr(expt) | Mr(calc) | Delta | Miss | Sequence |
|---|---|---|---|---|---|---|
| 199 - 217 | 1036.0417 | 2070.0688 | 2069.9688 | 0.1001 | 0 | R.SEGSSVNLSPPLEQCVPDR.G (Ions score 42) |
| 199 - 217 | 691.0425 | 2070.1057 | 2069.9688 | 0.1369 | 0 | R.SEGSSVNLSPPLEQCVPDR.G (Ions score 64) |
| 199 - 217 | 691.0472 | 2070.1198 | 2069.9688 | 0.1510 | 0 | R.SEGSSVNLSPPLEQCVPDR.G (Ions score 73) |
| 199 - 224 | 722.8864 | 2887.5165 | 2887.3519 | 0.1646 | 1 | R.SEGSSVNLSPPLEQCVPDRGQQYQGR.L (Ions score 22) |
| 199 - 224 | 963.5258 | 2887.5556 | 2887.3519 | 0.2037 | 1 | R.SEGSSVNLSPPLEQCVPDRGQQYQGR.L (Ions score 25) |
| 225 - 243 | 665.7327 | 1994.1763 | 1994.0408 | 0.1355 | 0 | R.LAVTTHGLPCLAWASAQAK.A (Ions score 33) |
| 225 - 243 | 665.7341 | 1994.1805 | 1994.0408 | 0.1397 | 0 | R.LAVTTHGLPCLAWASAQAK.A (Ions score 53) |

Fig. 10

```
  1  MAHVRGLQLP  GCLALAALCS  LVHSQHVFLA  PQQARSLLQR  VRRANTFLEE
 51  VRKGNLEREC  VEETCSYEEA  FEALESSTAT  DVFWAKYTAC  ETARTPRDKL
101  AACLEGNCAE  GLGTNYRGHV  NITRSGIECQ  LWRSRYPHKP  EINSTTHPGA
151  DLQENFCRNP  DSSTTGPWCY  TIDPTVRRQE  CSIPVCGQDQ  VTVAMTPRSE
201  GSSVNLSPPL  EQCVPDRGQQ  YQGRLAVTTH  GLPCLAWASA  QAKALSKHQD
251  FNSAVQLVEN  FCRNPDGDEE  GVWCYVAGKP  GDFGYCDLNY  CEEAVEEETG
301  DGLDEDSDRA  IEGRTATSEY  QTFFNPRTFG  SGEADCGLRP  LFEKKSLEDK
351  TERELLESYI  DGRIVEGSDA  EIGMSPWQVM  LFRKSPQELL  CGASLISDRW
401  VLTAAHCLLY  PPWDKNFTEN  DLLVRIGKHS  RTRYERNIEK  ISMLEKIYIH
451  PRYNWRENLD  RDIALMKLKK  PVAFSDYIHP  VCLPDRETAA  SLLQAGYKGR
501  VTGWGNLKET  WTANVGKGQP  SVLQVVNLPI  VERPVCKDST  RIRITDNMFC
551  AGYKPDEGKR  GDACEGDSGG  PFVMKSPFNN  RWYQMGIVSW  GEGCDRDGKY
601  GFYTHVFRLK  KWIQKVIDQF  GE
```

Fig. 11

```
         1          11         21         31         41         51
  1  MAHVRGLQLP GCLALAALCS LVHSQHVFLA PQQAPSLLQR VRRANTFLEE VRKGNLEREC   60
 61  VEETCSYEEA FEALESSTAT DVFWAKYTAC ETARTPRDKL AACLEGNCAE GLGTNYRGHV  120
121  NITRSGIECQ LWRSRYPHKP EINSTTHPGA DLQENFCRNP DSSTTGPWCY TTDPTVRRQE  180
181  CSIPVCGQDQ VTVAMTPRSE GSSVNLSPPL EQCVPDRGQQ YQGRLAVTTH GLPCLAWASA  240
241  QAKALSKHQD FNSAVQLVEN FCRNPDGDEE GVWCYVAGKP GDFGYCDLNY CEEAVEEETG  300
301  DGLDEDSDRA IEGRTATSEY QTFFNPRTFG SGEADCGLRP LFEKKSLEDK TERELLESYI  360
361  DGRIVEGSDA EIGMSPWQVM LFRKSPQELL CGASLISDRW VLTAAHCLLY PPMDKNFTEN  420
421  DLLVRIGKHS RTRYERNIEK ISMLEKIYIH PRYNWRENLD RDIALMKLKK PVAFSDYIHP  480
481  VCLPDRETAA SLLQAGYKGR VTGWGNLKET WTANVGKGQP SVLQVVNLPI VERPVCKDST  540
541  RIRITDNMFC AGYKPDEGKR GDACEGDSGG PFVMKSPFNN RWYQMGIVSW GEGCDRDGKY  600
601  GFYTHVFRLK KWIQKVIDQF GE
```

METHOD FOR MONITORING, DIAGNOSING, AND SCREENING CANCER THROUGH MEASURING THE CONCENTRATION OF DES-R PROTHROMBIN ACTIVATION PEPTIDE FRAGMENT F2 (DES-R F2) IN A SERUM

CROSS-REFERENCE TO RELATED APPLICATIONS

This application is a 371 of PCT/KR2009/001266 filed on Mar. 13, 2009, which claims the benefit of Korean Application No. 10-2008-0023803 filed on Mar. 14, 2008, the contents of each of which are incorporated herein by reference.

BACKGROUND OF THE INVENTION

1. Field of the Invention

The present invention relates to a protein marker for monitoring, diagnosis and screening of cancer, and a method for monitoring, diagnosis and screening of cancer using the same. More precisely, the invention relates to des-R-prothrombin activation peptide fragment F2 (des-R F2), the protein marker specifically down-regulated in liver cancer, breast cancer and stomach cancer patients, and a method for monitoring, diagnosis and screening of liver cancer, breast cancer and stomach cancer by the quantification of the said protein marker.

2. Description of the Related Art

Ever since Henry Bence-Jones first used the protein which was particularly precipitated in oxidized urine as a biomarker for diagnosis of multiple myeloma, numbers of tumor-related biomarkers (tumor markers, cancer markers, etc) have been developed and reported. The definition of a tumor marker is being broadened and thus different definitions have been suggested (Diamandis, E. P., et al., *AACC Press*, Washington D.C., pp. 3-8, 2002). However, there is a common definition of the tumor-related biomarker. That is, a tumor marker indicates a specific molecule, a material or a process that is changed in quantity or quality in pre-cancerous condition or cancerous lesions (Hayes D. F. et al., *J Natl Cancer Inst* 88, 1456-66, 1996). This change can be resulted from a tumor itself or from the response of normal tissues against the tumor.

In Korea, cancer incidence has increased gradually since 1970, and now cancer is the number one reason of death by disease. According to the report regarding cancer patients made by Korea National Health Insurance Cooperation in 2005, the most frequent incidence of cancer is stomach cancer, and colon cancer, lung cancer, liver cancer, and thyroid cancer followed in that order. Particularly, in male patients, stomach cancer is in the leading position and then lung cancer, liver cancer, colon cancer and prostate cancer follow, while in female patients thyroid cancer is in the leading position and then breast cancer, stomach cancer, colon cancer and lung cancer follow in that order. According to the above report, the death of cancer was 65,479 in total in 2005, indicating that cancer was recorded as the leading cause of death. Most cancers are found as progressed except prostate cancer and thyroid cancer and cure rate is around 50%. According to the research result of National Cancer Center Korea reported in 2003, direct cost paid by patients for the treatment of cancer reached 2.2 trillion won per year and if the productivity loss caused by early death and caregiver's loss was converted as costs, the total economic burden reached at least 15 trillion won per year. 56% of cancer patients lose their job after diagnosis of the disease, suggesting that cancer is the disease that damages not only personal health but also national economy greatly. In the meantime, stomach cancer demonstrates 90% of cure rate when it is early-diagnosed and breast cancer demonstrates 95% of survival rate when it is early-diagnosed. Therefore, early diagnosis of cancer not only improves cure rate significantly but also is very important in public health and national economy. Therefore, many countries make huge investment to develop a simple but accurate method for early-diagnosis. The method using prostate specific antigen (PSA) which has been used for diagnosis of prostate cancer as a marker is easy to measure PSA in serum and accordingly significantly reduces death caused by prostate cancer. Based on that, many researchers have tried to find out tumor-related biomarkers in serum.

Studies on tumor-related biomarkers (identification of a biomarker and validation thereof) are the processes that require a large amount of time and effort. There was a momentum in such studies, which was made by the completion of human genome project, high-density gene chip (DNA microarray) based techniques and proteome based high-throughput techniques.

It is well known that the method of genome analysis using gene chip plays an important role in understanding pathophysiology of cancer and identifying of a biomarker useful for diagnosis. However, the genome analysis method is critically limited because mRNA transcriptional activity cannot reflect the expression and functions of a target protein in tumor. Even though genetic information (DNA) is transcribed into RNA to produce protein, there are still numbers of complicated processes of diversity at the levels of RNA, protein translation and post-translational modification. Therefore, only when protein, the final product of DNA, is correctly analyzed (proteome), biological meaning of the target gene and corresponding protein in tumor development can be understood, the identification of a biomarker is realized, and an important clue for the development of a drug specific target can be provided.

Two-dimensional gel electrophoresis, MALDI-TOF MS (matrix-assisted laser desorption and ionization time-of-flight mass spectrometry) and SELDI-TOF (surface-enhanced laser desorption and ionization time-of-flight mass spectrometry) are the examples of recent high-throughput proteome analysis techniques. These techniques facilitate profiling of expression patterns of every protein and modified proteins in a wide range of molecular weights (Richter R. et al., *J Chromotogr B Biomed Sci Appl* 726, 2535, 1999; Paweletz C. P. et al., *Drug Dev Research* 49, 3442, 2000). SELDI-TOF MS is similar to MALDI-TOF MS, but is designed to be suitable for quantification with relatively high sensitivity and excellent reproducibility. Complicated biochemical materials can be treated by this technique and even a small amount of protein sample can also be used without purification. In addition, pre-treatment of a marker or matrix mixing processes are not necessary in this method. However, a novel marker that enables diagnosis of liver cancer, breast cancer and stomach cancer with higher accuracy and easiness is still required and a method using the same is also required.

The present inventors collected serum samples from liver cancer, breast cancer and stomach cancer patients and normal healthy people as well, followed by SELDI-TOF MS, protein sequencing, and bio-informatics analysis. As a result, the present inventors completed this invention by identifying protein markers useful for monitoring, diagnosing and screening liver cancer, breast cancer and stomach cancer.

SUMMARY OF THE INVENTION

It is an object of the present invention to provide protein markers for monitoring, diagnosis and screening of cancer, a method for monitoring, diagnosis and screening of cancer using the said protein marker, and a kit for monitoring, diagnosis, and screening of cancer using the same.

To achieve the above object, the present invention provides a kit for monitoring, diagnosis, and screening of cancer comprising a des-R prothrombin activation peptide fragment F2 (des-R F2) specific antibody.

The present invention also provides a detection method of des-R-prothrombin activation peptide fragment F2 for monitoring, diagnosis and screening of cancer, comprising the following steps:

1) measuring the expression of des-R-prothrombin activation peptide fragment F2 in a sample obtained from a subject; and 2) comparing the expression of des-R-prothrombin activation peptide fragment F2 of step 1) with that of a normal subject, and then selecting subjects demonstrating reduced des-R-F2 expression.

The present invention further provides a biochip for monitoring, diagnosis, and screening of cancer, on which des-R-prothrombin activation peptide fragment F2 specific biomolecules are integrated on a solid substrate.

The present invention also provides a use of des-R-prothrombin activation peptide fragment F2 for the construction of a kit for monitoring, diagnosis, and screening of cancer.

In addition, the present invention provides a use of des-R-prothrombin activation peptide fragment F2 for the construction of a biochip for monitoring, diagnosis, and screening of cancer.

Advantageous Effect

The des-R-prothrombin activation peptide fragment F2 (des-R F2) of the present invention is down-regulated specifically in body fluids of liver cancer, breast cancer and stomach cancer patients. Thus, it is possible to screen and early-diagnose liver cancer, breast cancer and stomach cancer, simply by measuring the expression of the protein, leading to the increase of survival rate of liver cancer, breast cancer, and stomach cancer patients by early diagnosis followed by quick treatment response and further to the decrease of continued national loss by cancer treatment.

BRIEF DESCRIPTION OF THE DRAWINGS

The application of the preferred embodiments of the present invention is best understood with reference to the accompanying drawings, wherein:

FIG. 9 is a diagram illustrating the result of ESI-Q-TOF MS/MS of 12.5 kDa peak protein.

FIG. 10 is a diagram illustrating the amino acid residue of prothrombin precursor (P00734), the product from 12.5 kDa peak protein after N-terminal sequencing.

FIG. 11 is a diagram illustrating the total amino acid sequence of 12.5 kDa peak protein (des-R F2).

DETAILED DESCRIPTION OF THE INVENTION

Figure 1:
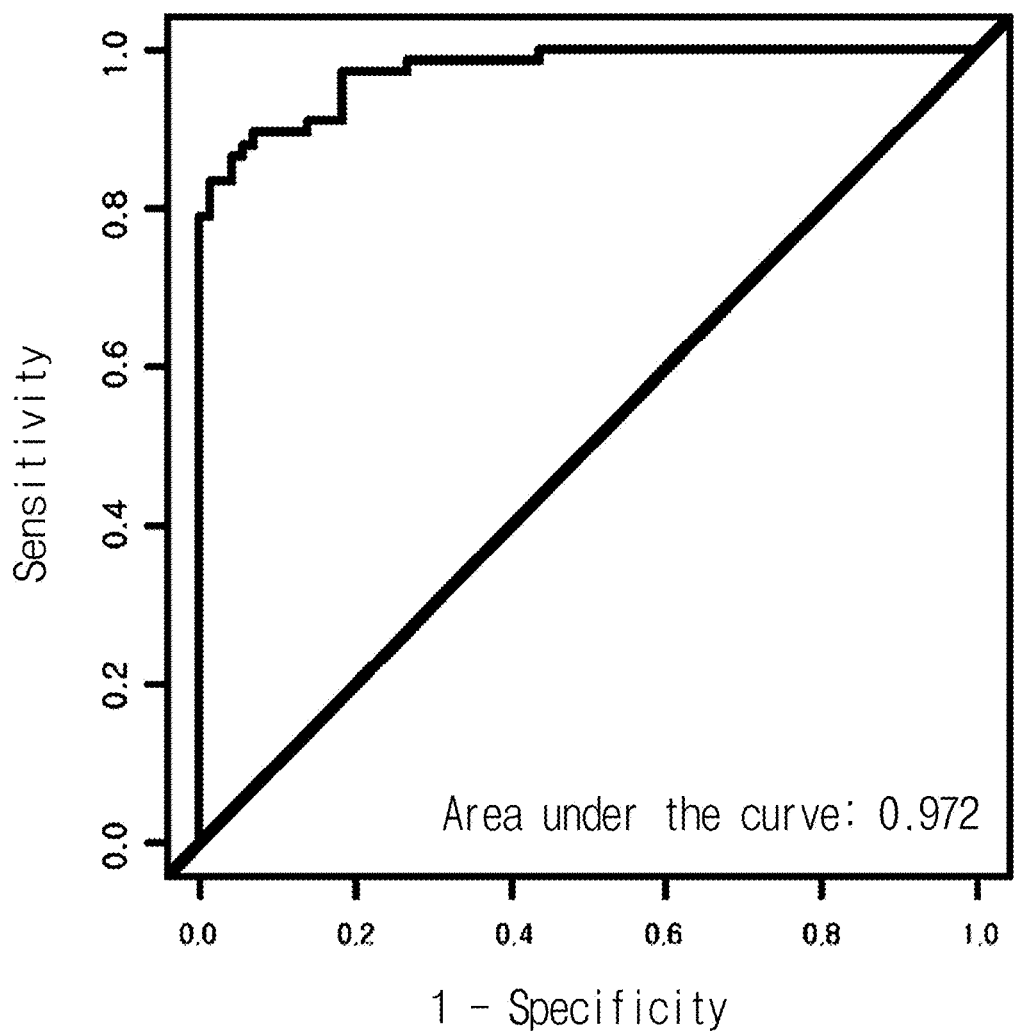
FIG. 1 is a ROC (receiver operating characteristic) curve illustrating the result of spectrum analysis with serum of a liver cancer patient.
Figure 2:
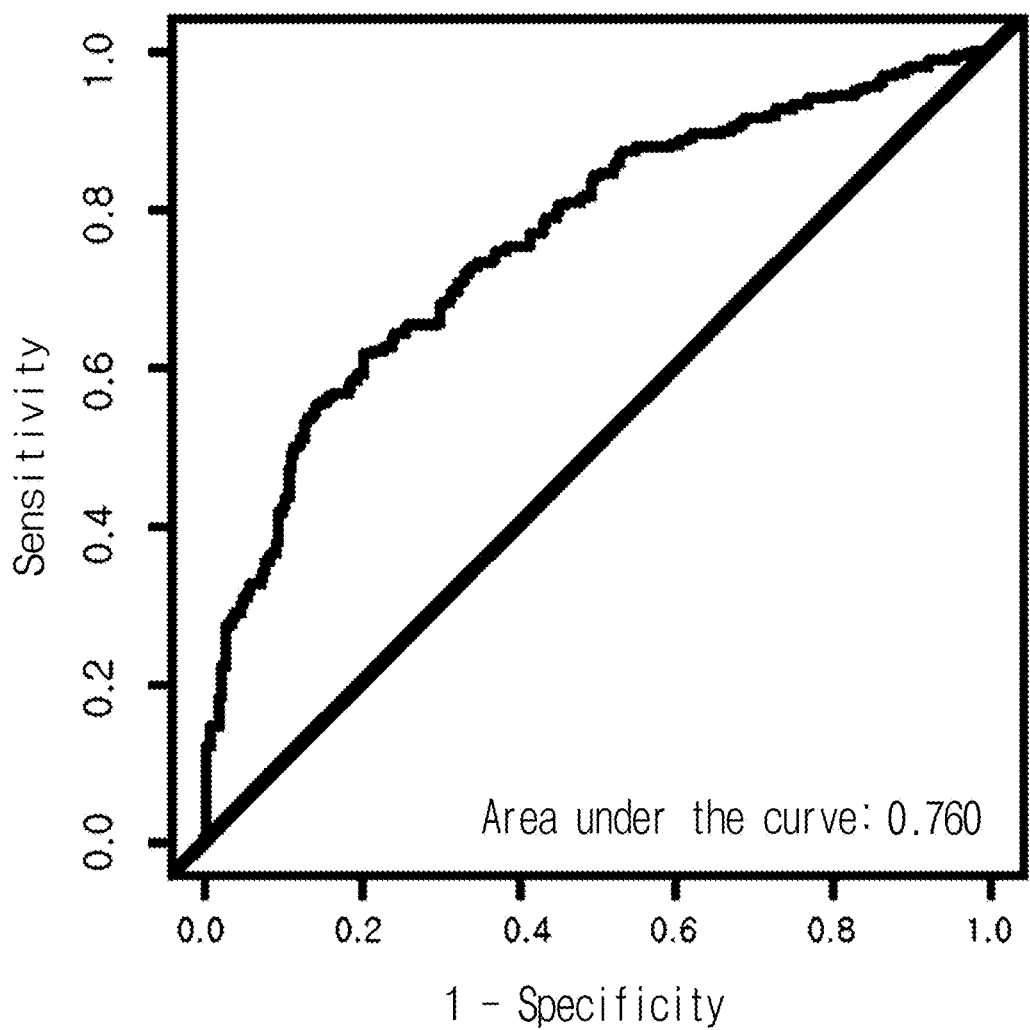
FIG. 2 is a ROC (receiver operating characteristic) curve illustrating the result of spectrum analysis with serum of a stomach cancer patient.
Figure 3:
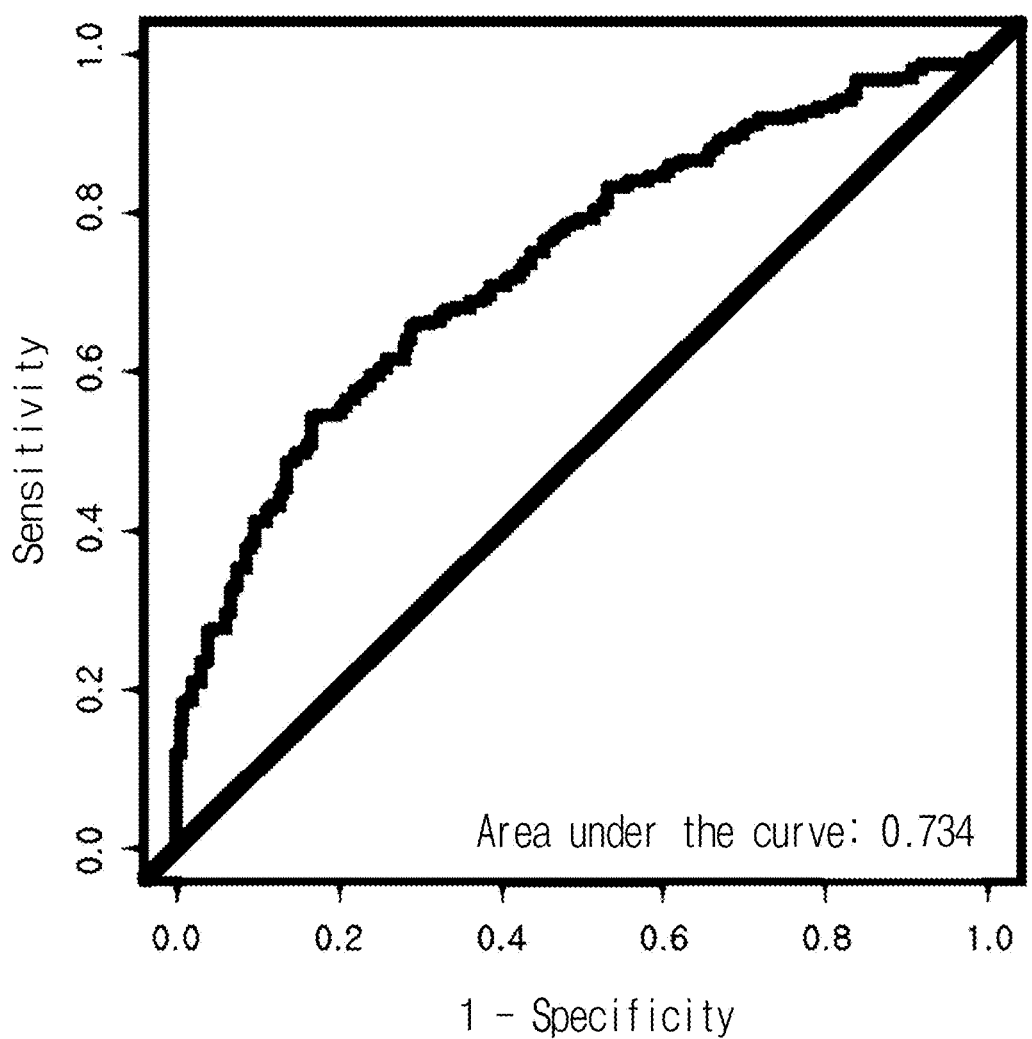
FIG. 3 is a ROC (receiver operating characteristic) curve illustrating the result of spectrum analysis with serum of a breast cancer patient.
Figure 4:
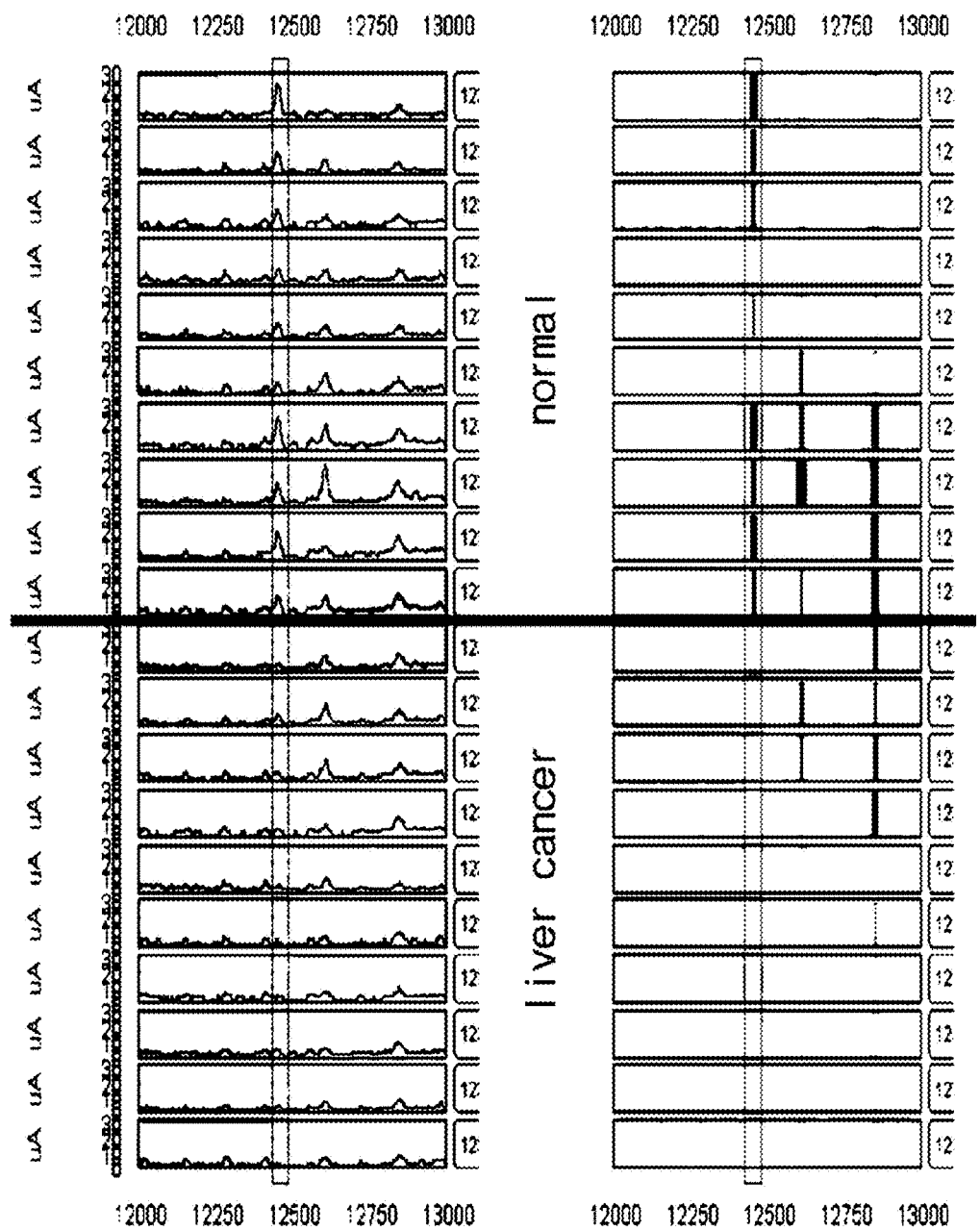
FIG. 4 is a diagram illustrating the comparison of spectrums between serums of a normal subject and a liver cancer patient.
Figure 5:
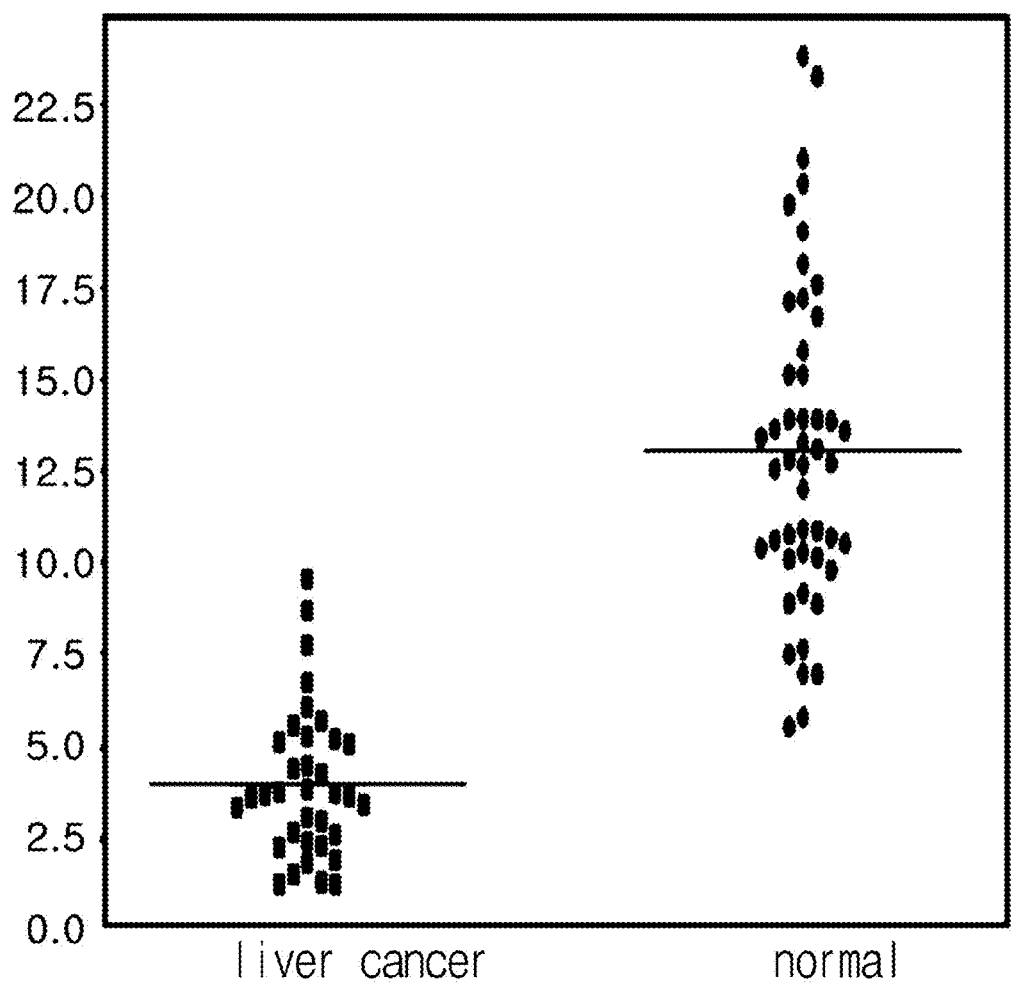
FIG. 5 is a graph showing scattering degree illustrating that 12.5 kDa peak is reduced in liver patient serum, compared with that in a normal subject, resulted from serum spectrum analysis.
Figure 6:
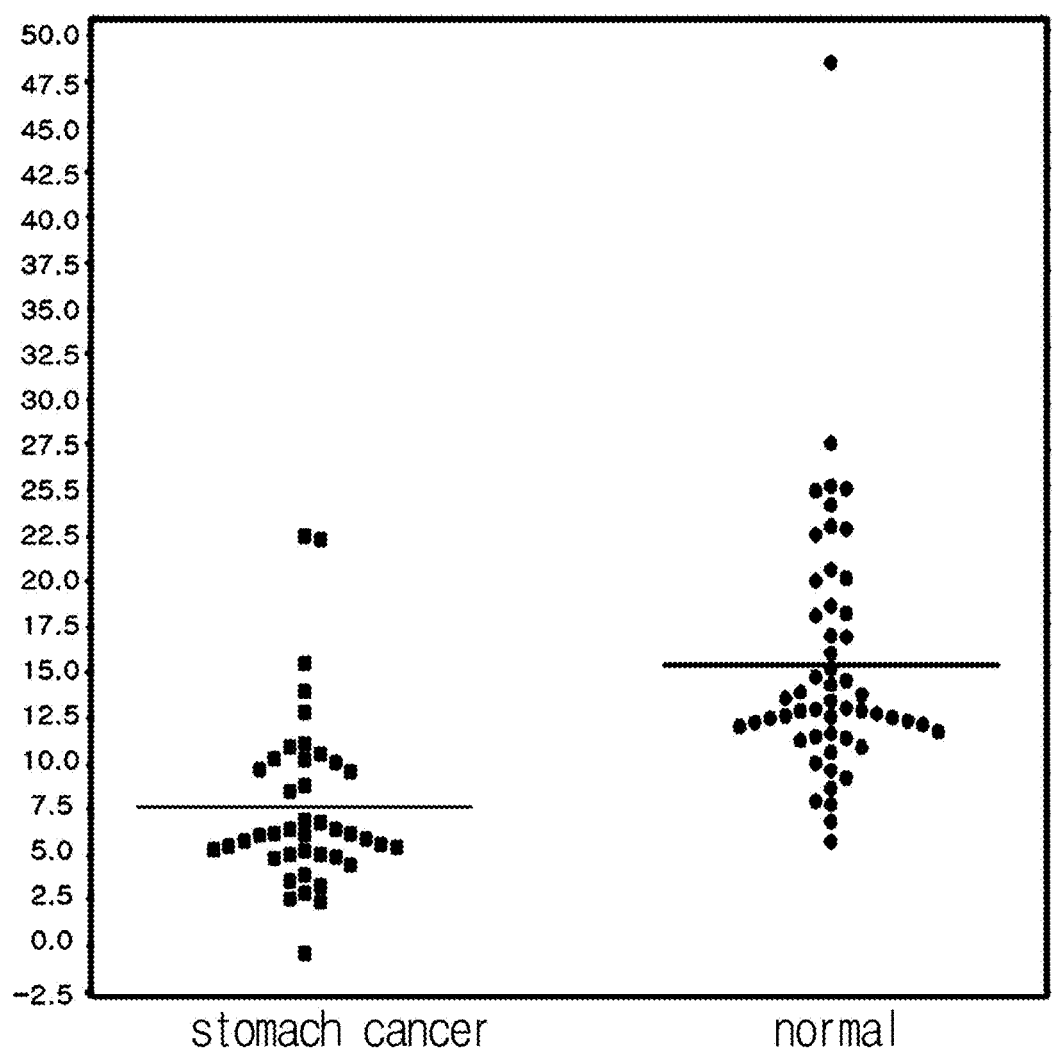
FIG. 6 is a graph showing scattering degree illustrating that 12.5 kDa peak is reduced in stomach cancer patient serum, compared with that in a normal subject, resulted from serum spectrum analysis.
Figure 7:
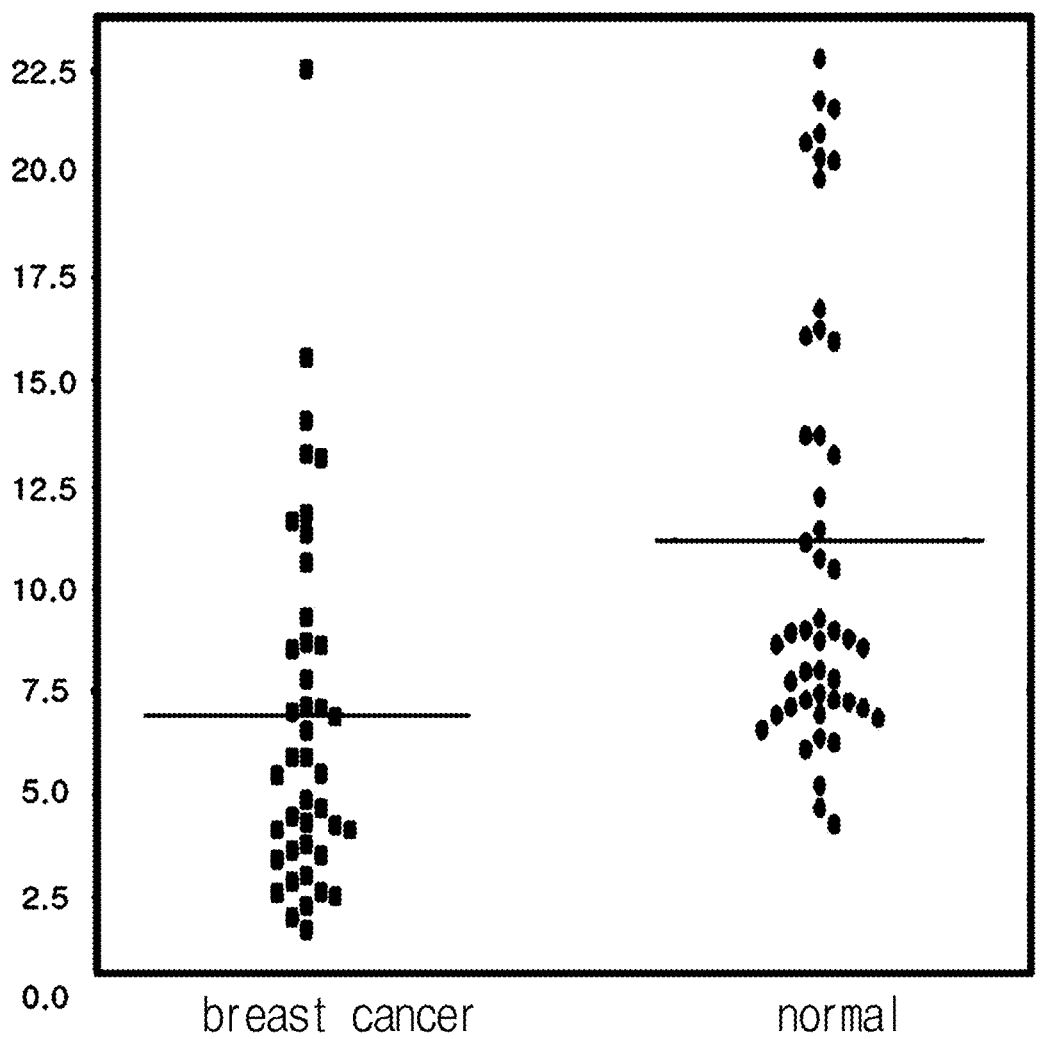
FIG. 7 is a graph showing scattering degree illustrating that 12.5 kDa peak is reduced in breast patient serum, compared with that in a normal subject, resulted from serum spectrum analysis.

Hereinafter, the present invention is described in detail.

The present invention provides a kit for monitoring, diagnosis, and screening of cancer comprising a des-R-prothrombin activation peptide fragment F2 (des-R F2) specific antibody.

The said des-R-prothrombin activation peptide fragment F2 preferably consists of the amino acid sequence represented by SEQ. ID. NO: 1, but not always limited thereto.

The des-R prothrombin activation peptide fragment F2 preferably contains an epitope comprising the amino acid sequence represented by SEQ. ID. NO: 2 (Ser Glu Gly Ser Ser Val Asn Leu Ser Pro Pro Leu) at N-terminal region and containing another epitope comprising the amino acid sequence represented by SEQ. ID. NO: 3 (Gly Leu Asp Glu Asp Ser Asp Arg Ala Ile Glu Gly) at C-terminal region, but not always limited thereto.

The des-R-prothrombin activation peptide fragment F2 of the present invention is preferably down-regulated in a subject with cancer, but not always limited thereto.

The said cancer herein is preferably liver cancer, breast cancer or stomach cancer, but not always limited thereto.

The said antibody is preferably bound specifically to the epitope corresponding to the carboxyl terminal of des-R-prothrombin activation peptide fragment F2, but not always limited thereto.

The kit of the present invention can be used for measuring the protein marker des-R F2 which shows different expression patterns in a subject with cancer and a normal subject. The kit of the present invention not only facilitates monitoring, diagnosis, and screening of cancer but also makes it possible to modify cancer treatment according to the result of monitoring the individual response to the treatment.

The antibody included in the kit can be a polyclonal antibody, a monoclonal antibody and a fragment being able to bind with an epitope, etc.

The polyclonal antibody can be prepared by the conventional processes of injecting the protein marker des-R F2 into an animal; drawing blood from the animal; and obtaining serum containing the antibody from the blood sample. Such polyclonal antibody can be purified by any conventional method known to those in the art and be produced by using any animal model, for example goat, rabbit, sheep, monkey, horse, pig, cow, and dog, as a host.

The monoclonal antibody can be prepared by any technique used for producing antibody molecule through continuous culture, which is exemplified by hybridoma technique, human B-cell hybridoma technique, and EBV-hybridoma technique, but not always limited thereto (Kohler G et al., *Nature* 256:495-497, 1975; Kozbor D et al., *J Immunol Meth-*

*ods* 81:31-42, 1985; Cote R J et al., *Proc Natl Acad Sci* 80:2026-2030, 1983; and Cole S P et al., *Mol Cell Biol* 62:109-120, 1984).

An antibody fragment that harbors the marker protein specific binding site can be prepared. For example, F(ab')2 fragment can be prepared by decomposing an antibody molecule with pepsin. Fab fragment can be prepared by reducing the disulfide bridge of F(ab')2. In addition, Fab expression library can be constructed, by which a specific monoclonal Fab fragment can be identified fast and easy (Huse W D et al., *Science* 254: 1275-1281, 1989).

The said antibody can be fixed on a solid substrate to make washing or conjugate separation process easy. The solid substrate is exemplified by synthetic resin, nitrocellulose, glass plate, metal plate, glass fiber, microspheres and microbeads. The synthetic resin herein is exemplified by polyester, polyvinyl chloride, polystyrene, polypropylene, PVDF and nylon. In this invention, to fix a maker protein specific antibody on a solid substrate, microspheres are suspended, which are transferred in a microtube. The supernatant is discarded by centrifugation, followed by resuspension. N-hydroxy-sulfosuccinimide and 1-ethyl-3-(3-dimethylaminopropyl)-carbodiimide hydrochloride are treated thereto stepwise. The supernatant is discarded again by centrifugation, followed by washing and storing.

In the case that a sample obtained from a patient is contacted with the marker protein specific antibody fixed on a solid substrate, the sample can be diluted properly before the contact.

The kit of the present invention also includes an antibody for detection that is specifically bound to the marker protein. The antibody for detection can be a conjugate labeled with a coloring enzyme, a fluorescent material, a radioisotope or a colloid, and specifically a marker protein specific primary antibody is preferred. The coloring enzyme is exemplified by peroxidase, alkaline phosphatase or acid phosphatase (ex: horseradish peroxidase); and the fluorescent material is exemplified by fluorescein carboxylic acid (FCA), fluorescein isothiocyanate (FITC), fluorescein thiourea (FTH), phycoerythrin(PE), 7-acetoxycoumarin-3-yl, fluorescein-5-yl, fluorescein-6-yl, 2',7'-dichloro fluorescein-5-yl, 2',7'-dichloro fluorescein-6-yl, dihydrotetramethylrhodamine-4-yl, tetramethylrhodamine-5-yl, tetramethylrhodamine-6-yl, 4,4-difluoro-5,7-dimethyl-4-bora-3a,4a-diaza-s-indacen-3-ethyl, 4,4-difluoro-5,7-diphenyl-4-bora-3 or 4a-diaza-s-indacen-3-ethyl.

The kit of the present invention can additionally contain (1) an antibody for detection that is specifically bound to the marker and (2) a ligand that is specifically bound to the said antibody for detection. The ligand herein can be a secondary antibody that is specifically bound to protein A or the antibody for detection. The ligand can also be a conjugate labeled with a marker such as a coloring enzyme, a fluorescent material, a radioisotope or a colloid. The antibody for detection herein is preferably the biotinylated primary antibody or the primary antibody treated with digoxigenin for the ligand, but the treatment method of the antibody for detection is not limited thereto. To bind the ligand to the antibody for detection, streptavidin or avidin is preferably used as the ligand, but not always limited thereto. In a preferred embodiment of the present invention, streptavidin labeled with fluorescent material was used as the ligand and the biotinylated primary antibody was used for the ligand as the antibody for detection.

The kit of the present invention is suitable for detecting the amount of the antibody for detection after treating the antibody for detection to the said antibody-marker conjugate, with facilitating monitoring, diagnosis, and screening of cancer. The antibody for detection and the ligand are treated to the antibody-marker conjugate stepwise and then the amount of the antibody for detection is measured, leading to diagnosis and screening of cancer. In this invention, the antibody for detection was incubated with a washed antibody-marker conjugate, followed by washing. Then, the antibody for detection was quantified to measure the amount of the marker. Quantification or detection of the antibody for detection can be performed by using fluorescence, iluminescence, chemiluminescence, optical density, reflection or transmission.

High throughput screening (HTS) system is preferably used for screening the antibody for detection or the ligand. For the system, fluorescence assay performed by measuring fluorescence from the fluorescein labeled antibody or radio assay performed by measuring radiation from the isotope labeled antibody; SPR (surface plasmon resonance) measuring changes of plasmon resonance on the surface without using a detector or SPRI (surface plasmon resonance imaging) can be preferably used, but not always limited thereto.

Fluorescence assay is the method to confirm a signal by spotting using fluorescence scanner program after labeling the antibody for detection with a fluorescent material. This method is useful for confirming the binding strength. The fluorescent material herein is preferably selected from the group consisting of Cy3, Cy5, poly L-lysine-fluorescein isothiocyanate (FITC), rhodamine-B-isothiocyanate (RITC) and rhodamine, but not always limited thereto. Unlike fluorescence assay, SPR system facilitates real time analysis of antibody binding strength without labeling the sample with a fluorescent material. But, this method has a disadvantage that simultaneous large scale analysis is not possible. SPRI enables simultaneous large scale analysis of samples using microarray but has a disadvantage of low detection sensitivity.

The kit of the present invention additionally includes washing buffer or eluent that can hold the antibody conjugated marker alone after eliminating substrate and non-conjugated protein. The kit also contains biological sample such as serum, urine, tear, and saliva, from which disease specific polypeptide that is distinguished from normal ones can be confirmed. For the biological sample, biological fluid such as blood, serum, and plasma are preferred and serum is more preferred. The sample can be manipulated in order to increase detection sensitivity of a marker. For example, serum obtained from a patient can be pretreated by anion exchange chromatography, affinity chromatography, size exclusion chromatography, liquid chromatography, sequential extraction or gel electrophoresis, etc, but not always limited thereto.

To identify biomarkers useful for cancer diagnosis, the present inventors obtained serums from patients diagnosed with liver cancer, breast cancer, and stomach cancer and from normal subjects, followed by protein analysis using SELDI-TOF MS (surface-enhanced laser desorption and ionization time-of-flight mass spectrometry). The protein analysis herein is preferably performed with SELDI-TOF MS (surface-enhanced laser desorption/ionization time-of-flight mass spectrometry), MALDI-TOF MS (Matrix-assisted laser desorption/ionization time-of-flight mass spectrometry) or ESI-Q-TOF MS (electrospray-quadrupole-time of flight mass spectrometry), but not always limited thereto (Richter R. et al., *J Chromotogr B Biomed Sci* Appl 726, 2535, 1999; Paweletz C. P. et al., *Drug Dev Research* 49, 3442, 2000). Mann-Whitney U-test p-value and AUC (area under the receiver operating characteristic curve) of produced peaks were compared between the normal group and the cancer patient group. As a result, among all peaks, 12.5 kDa peak (12,451 m/z) was peculiarly reduced in three types of cancer patients, even though the reduction rate varied, unlike in the normal group. It was confirmed that the average reduction rate of the peak was greater in liver cancer, followed by stomach cancer and breast cancer in that order, compared with that of the normal group (see Table 1, FIGS. 1-7).

To isolate SELDI-TOF MS peak protein that showed significant changes in liver cancer, breast cancer and stomach cancer patients, the present inventors performed chromatography and 2-dimensional electrophoresis with serum. The chromatography herein is preferably ion-exchange chromatography and hydrophobic chromatography, but not always limited thereto.

To identify SELDI-TOF MS peak protein that showed significant changes in liver cancer, breast cancer, and stomach cancer patients, the present inventors performed staining and elution of the protein fraction isolated by the above chromatography and 2-dimensional electrophoresis, followed by ESI-Q-TOF MS/MS and N-terminal amino acid sequencing. As a result, the amino acid residue sequence, Ser-Glu-Gly-Ser-Ser-Val-Asn (SEQ. ID. NO: 4), was identified. This sequence corresponds to the amino acid residue 199-205 of prothrombin precursor (P00734), and this region is N-terminal of prothrombin activation peptide fragment F2. The total amino acid sequence was confirmed from the results of ESI-Q-TOF MS/MS and N-terminal amino acid sequencing. As a result, the fragment was confirmed to be des-R-prothrombin activation peptide fragment F2 (des-R F2) that lost C-terminal arginine from the prothrombin activation peptide fragment F2. The molecular weight theoretically calculated (12,457 Da) was consistent with the peak found in SELDI-TOF MS (12,451 m/z) (see FIGS. 8-11). The sequence of des-R-prothrombin activation peptide fragment F2 is as follows:

```
                                        (SEQ. ID. NO: 1)
Ser Glu Gly Ser Ser Val Asn Leu Ser Pro Pro Leu Glu

Gln Cys Val Pro Asp Arg Gly Gln Gln Tyr Gln Gly Arg

Leu Ala Val Thr Thr His Gly Leu Pro Cys Leu Ala Trp

Ala Ser Ala Gln Ala Lys Ala Leu Ser Lys His Gln Asp

Phe Asn Ser Ala Val Gln Leu Val Glu Asn Phe Cys Arg

Asn Pro Asp Gly Asp Glu Glu Gly Val Trp Cys Tyr Val

Ala Gly Lys Pro Gly Asp Phe Gly Tyr Cys Asp Leu Asn

Tyr Cys Glu Glu Ala Val Glu Glu Glu Thr Gly Asp Gly

Leu Asp Glu Asp Ser Asp Arg Ala Ile Glu Gly
```

The present invention also provides a detection method of des-R-prothrombin activation peptide fragment F2 for monitoring, diagnosis and screening of cancer, comprising the following steps:

1) measuring the expression of des-R-prothrombin activation peptide fragment F2 (des-R F2) in the sample obtained from a subject; and 2) comparing the expression of des-R-prothrombin activation peptide fragment F2 of step 1) with that of a normal subject, and then selecting subjects demonstrating reduced des-R-F2 expression.

In this method, the des-R-prothrombin activation peptide fragment F2 of step 1) is preferably composed of the amino acid sequence represented by SEQ. ID. NO: 1, but not always limited thereto. The said des-R-prothrombin activation peptide fragment F2 preferably contains an epitope having the amino acid sequence represented by SEQ. ID. NO: 2 in N-terminal region and another epitope having the amino acid sequence represented by SEQ. ID. NO: 3 in C-terminal region, but not always limited thereto.

In this method, the sample of step 1) is preferably blood, serum or plasma, and serum is more preferred, but not always limited thereto.

In this method, the expression of step 1) is measured preferably by 2-dimensional gel electrophoresis, MALDI-TOF MS (matrix-assisted laser desorption and ionization time-of-flight mass spectrometry) or SELDI-TOF MS (surface-enhanced laser desorption and ionization time-of-flight mass spectrometry), but not always limited thereto.

In this method, the selection of step 2) takes advantages of bioinformatics techniques. Particularly, the expression of each protein marker is compared between a normal individual and a subject. Then, the subject showing down-regulated expression is selected. The analysis method based on bioinformatics is described in Korean Patent No. 0679173.

In this method, the cancer of step 2) is preferably liver cancer, breast cancer or stomach cancer, but not always limited thereto.

When the protein marker of the present invention is used, the analysis is preferably performed by the following procedure. Target serum proteome for the diagnosis of cancer is inputted, followed by analysis based on bioinformatics. Expression patterns of des-R F2, the disease specific marker protein, of a normal subject and a sample serum are converted as numeral values and then compared each other. Based on the comparison, the target serum proteome is judged as normal or cancer, suggesting that monitoring, diagnosis, and screening of cancer can be possible by that.

The present invention further provides a biochip for monitoring, diagnosis, and screening of cancer, on which des-R-prothrombin activation peptide fragment F2 specific biomolecules are integrated on a solid substrate.

The biomolecule herein is preferably an antibody or an aptamer, but not always limited thereto.

The solid substrate herein is preferably selected from the group consisting of plastic, glass, metal and silicon, but not always limited thereto.

The cancer herein is preferably liver cancer, breast cancer, or stomach cancer, but not always limited thereto.

Particularly, when the protein marker of the present invention is used, the analysis is preferably performed by the following procedure. Target serum proteome for the diagnosis of cancer is inputted, followed by analysis based on bioinformatics. Expression patterns of des-R F2, the disease specific marker protein, of a normal subject and a sample serum are converted as numeral values and then compared each other. Based on the comparison, the target serum proteome is judged as normal or cancer, suggesting that monitoring, diagnosis, and screening of cancer can be possible by that.

The present invention also provides a use of des-R-prothrombin activation peptide fragment F2 for the construction of a kit for monitoring, diagnosis, and screening of cancer.

In addition, the present invention provides a use of des-R-prothrombin activation peptide fragment F2 for the construction of a biochip for monitoring, diagnosis, and screening of cancer.

The cancer herein is preferably liver cancer, breast cancer, or stomach cancer, but not always limited thereto.

The des-R-prothrombin activation peptide fragment F2 of the present invention is down-regulated specifically in a subject with liver cancer, breast cancer or stomach cancer, compared with in a normal subject. Therefore, this fragment can be used as a marker protein for the production of a kit or a biochip for monitoring, diagnosis, and screening of liver cancer, breast cancer or stomach cancer.

DESCRIPTION OF THE PREFERRED EMBODIMENTS

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLE 1

Obtainment and Preservation of Serum

In this invention, three test groups were prepared; group 1 with 71 normal subjects (29 women, 42 men) and 66 liver cancer patients (14 women, 52 men); group 2 with 250 normal subjects (119 women, 131 men) and 245 stomach cancer patients (84 women, 161 men); and group 3 with 196 normal subjects (196 women) and 252 breast cancer patients (252 women).

The age of the normal subjects in group 1 for the liver cancer related experiment ranged from 29 to 64 (mean: 46.9, median: 47), and the age of the liver cancer patients ranged from 35 to 75 (mean: 57.1, median: 58). The age of the normal subjects in group 2 for stomach cancer related experiment ranged from 23 to 67 (mean: 45.7, median: 45) and the age of the stomach cancer patients ranged from 28 to 86 (mean: 59.1, median: 61). Cancer stages of those who had stomach cancer were as follows: stage 1, 129 patients; stage 2, 48 patients; stage 3, 36 patients; and stage 4, 32 patients. In the case of breast cancer related experiment, participants were all female and the age of the normal subjects ranged from 23 to 71 (mean: 46.5, median: 45) and the age of the breast cancer patients ranged from 21 to 82 (mean: 47.5, median: 47). Cancer stages of stomach cancer patients were as follows: stage 0, 17 patients; stage 1, 71 patients; stage 2, 104 patients; stage 3, 50 patients; and stage 4, 10 patients.

Five ml and of peripheral blood was drawn from each of normal subjects, liver cancer, breast cancer, and stomach cancer patients using vacutainer SST II tube (Becton Dickinson), which stood at room temperature for one hour. Centrifugation was performed at 1500 g for 10 minutes and supernatant was obtained. Serum was taken from the supernatant and stored at −80 until use.

EXAMPLE 2

Serum Protein Analysis

Serum was analyzed by anion exchange (Q10) proteinchip array (Ciphergen). Particularly, 10 µl of serum was diluted with 15 µl of solubilization buffer (9 M Urea, 2% CHAPS), which stood at room temperature for 30 minutes. 45 µl of Q10 binding buffer (0.05% Triton X-100 in 50 mM HEPES, pH 7.0) was added to 5 µl of the diluted serum sample, followed by mixing with vortex. To equilibrate Q10 chip, 10 µl of binding buffer was loaded on every spot, which stood at room temperature for 5 minutes. After eliminating binding buffer, 10 µl of fresh binding buffer was loaded on each spot again, which stood at room temperature for 5 minutes. 5 µl of serum mixture (serum sample+solubilization buffer+binding buffer) was loaded on each spot, followed by reaction in a humidify chamber at room temperature for 1 hour. After eliminating serum mixture, 10 µl of binding buffer was loaded and then binding buffer was rightly eliminated (repeated 4 times). After eliminating binding buffer, 5 µl of HPLC water was loaded thereto. HPLC water was then eliminated (repeated twice). The chip was dried at room temperature. 1 µl of SPA solution (5 mg of sinapinic acid in 50% acetonitrile and 0.5% trifluoroacetic acid) was loaded on the dried spot. When SPA was dried, 1 µl of the solution was loaded again. When the spot was completely dried, the chip proceeded to Protein-Chip System Series 4000 (Ciphergen Biosystems Inc., Fremont, Calif., USA), and spectrum was obtained. At that time, conditions were as follows; Focus mass: 15,000, laser energy: 3000 nJ, 265 shots, 1000-200000 Da mass range.

EXAMPLE 3

Spectrum Analysis

Mass calibration was performed according to external calibration using a calibrant such as bovine superoxide dismutase, equine myoglobin, bovine beta-lactoglobulin A and horseradish peroxidase (Ciphergen Biosystems Inc., Fremont, Calif., USA), followed by normalization using total ion current. Automatic peak detection was performed using Ciphergen Express Client ver. 3.0 software (signal-to-noise: 5 or up, valley depth: 5 or up, minimum peak threshold: 0%, cluster mass window: 0.3% MW). As a result, 203 peak clusters in total were confirmed. Mann-Whitney U-test p-value and AUC (area under the receiver operating characteristic curve) of the peaks were compared between normal and cancer groups.

As a result, among all peaks, the expression pattern of 12.5 kDa peak (12,451 m/z) was significantly different in three cancer groups, from that of the normal group. As shown in Table 1, the peak was reduced in cancer groups, even though the reduction rate varied, compared with in the normal group. The average reduction rate in each cancer group to that of the normal group was as follows; 0.57 in stomach cancer, 0.67 in breast cancer and 0.31 in liver cancer. So, the peak was most reduced in liver cancer and stomach cancer and breast cancer followed. AUC of each cancer was as follows; 0.76 in stomach cancer, 0.73 in breast cancer and 0.97 in liver cancer (FIGS. 1-7).

TABLE 1

|  | Average (cancer) | Average (normal) | Average (cancer)/Average (normal) | p-value |
|---|---|---|---|---|
| Liver cancer | Liver cancer patient n = 66 | Normal subject n = 71 | — | — |
|  | 4.14 | 13.21 | 0.31 | $1.56 \cdot 10^{-21}$ |
| Stomach cancer | Stomach patient n = 245 | Normal subject n = 250 | — | — |
|  | 11.14 | 19.39 | 0.57 | $1.16 \cdot 10^{-23}$ |
| Breast cancer | Breast cancer patient n = 252 | Normal subject n = 196 | — | — |
|  | 6.93 | 10.31 | 0.67 | $1.73 \cdot 10^{-17}$ |

EXAMPLE 4

Separation of 12,451 m/z Protein

<4-1> Preparation of Heat Resistant Serum Sample 50 and of 0.2 M Tris-HCl (pH 9.0) (including 7% PEG 6000 (Merck) and 20 mM EDTA) and 50 ml and of pooled human serum (Serologicals Corporation, Norcross, Ga., USA) were mixed at the ratio of 1:1. Water was boiled in a 1 l beaker at 100. The mixture was loaded into four 50 ml and tubes (25 ml and each), followed by boiling at 100 for 10 minutes. Tubes were taken out every 2 minutes for vortex mix. After 10 minute standing at room temperature, the mixture proceeded to centrifugation at 3,000 rpm for 15 minutes to separate supernatant. If there were floats, the supernatant was filtered and proceeded to chromatography. As a result, 50-60 ml of boiled serum was obtained.

<4-2> Ion Exchange Chromatography 100 mM sodium phosphate and 50 mM citric acid were mixed at the ratio of 4.6:5.4 to prepare buffer (pH 4.5-6.0). The boiled serum was diluted with the buffer at the ratio of 1:2 (boiled serum 50 ml+buffer 100 ml=150 ml). 2 ml of Q-Sepharose Fast Flow resin (Sigma Q1126) was packed in four 10 ml centrifugation columns (Handee™ Centrifuge Columns (PIERCE)). Centrifugation was performed with the packed columns with 1,000 g-force for 2 minutes to spin out preserving solution. Pre-equilibration of beads was performed using 4 ml of the prepared buffer (2~3 times). The boiled diluted serum was bound to the column for 20 minutes (12.5 ml/column). The column was centrifuged at 1000 g to remove unbound proteins. The boiled serum remaining in the column was bound again by 12.5 ml each for 20 minutes. Centrifugation was performed again at 1,000 g for 2 minutes to eliminate unbound proteins. The boiled serum remaining in the column was bound again by 12.5 ml each for 20 minutes. Centrifugation was performed again at 1,000 g for 2 minutes to eliminate unbound proteins. Anion exchange resin was washed with the buffer first prepared above, twice for 5 minutes each time. The protein bound to anion exchange resin was eluted with 3 ml of 1% TFA 4 times for 10 minutes. Fractions obtained from each stage were placed on Au-chip and confirmed by SELDI-TOF.

<4-3> Hydrophobic Chromatography

Octyl-Sepharose CL 4B resin (Sigma 06001) was packed in 2 centrifugation columns, 2 ml each, followed by centrifugation at 1,000 g for 2 minutes to remove preserving solution. Hydrophobic resin was pre-equilibrated with 4 ml of 1% TFA (2-3 times). The fractions eluted with 1% TFA were bound on the column packed with the hydrophobic resin, 12 ml each, for 20 minutes. Centrifugation was performed at 1,000 g for 2 minutes to spin out unbound proteins. The fractions remaining in the same column were bound again by 12 ml each for 20 minutes. Centrifugation was performed again at 1,000 g for 2 minutes to eliminate non-reacted proteins. The hydrophobic resin was washed three times with 0.1% TFA/10% ACN solution for 5 minutes. After washing, proteins bound on the hydrophobic resin were eluted with 3 ml of 0.1% TFA/50% ACN 4 times for 10 minutes. The eluted fractions were concentrated to make the total volume 1 ml using freeze drier for FPLC separation.

<4-4> Hydrophobic Chromatography (FPLC System, C8 20 ml Column)

Separation was performed with C8 column (HiPrep 16/10 Octyl FF column (Amersham)) using buffer A (0.1% TFA) and buffer B (0.1% TFA/80% ACN) system. First, protein was bound using 0.1% TFA for 13 minutes. Second, ACN was graded from 0 to 50% for 25 minutes. Third, 50% ACN was spilled isocratically for 15 minutes. At last, washing was performed with 80% ACN for 20 minutes. At that time, flow rate was 2 ml/min. The fractions obtained from each stage were placed on Au-chip, followed by confirmation with SELDI-TOF. M/z 12,451 peak was confirmed in the stage of 50% ACN elution. The confirmed fractions were collected and dried with freeze-drier. To eliminate TFA and ACN remaining in the fractions, complete-drying/dissolving using HPLC D.W was repeated 10 times, followed by confirmation using pH paper. The dried samples were dissolved in 200 μl of D.W and stored at −70.

<4-5> 2-dimensional Electrophoresis

40 μl of the stored sample was mixed with 10 μl of 10% SDS. The mixture was mixed with 220 μl of 1.1× rehydration buffer (8.8 M Urea, 4.4% CHAPS, 0.55% IPG buffer, BPB). 260 μl of the mixture was loaded on pH 4-7 13 cm strip. Conditions of isoelectric focusing (IEF) are as shown in Table 2.

TABLE 2

|  | Voltage (V) | Time (hr) |
|---|---|---|
| Rehydration | 30 | 10 |
| Desalting | 500 | 1 |
| Desalting | 1000 | 1 |
| Step-n-hold | 3000 | 1 |
| Step-n-hold | 5000 | 2 |
| Gradient | 8000 | 2 |
| Step-n-hold | 8000 | 4.5 |

Figure 8:
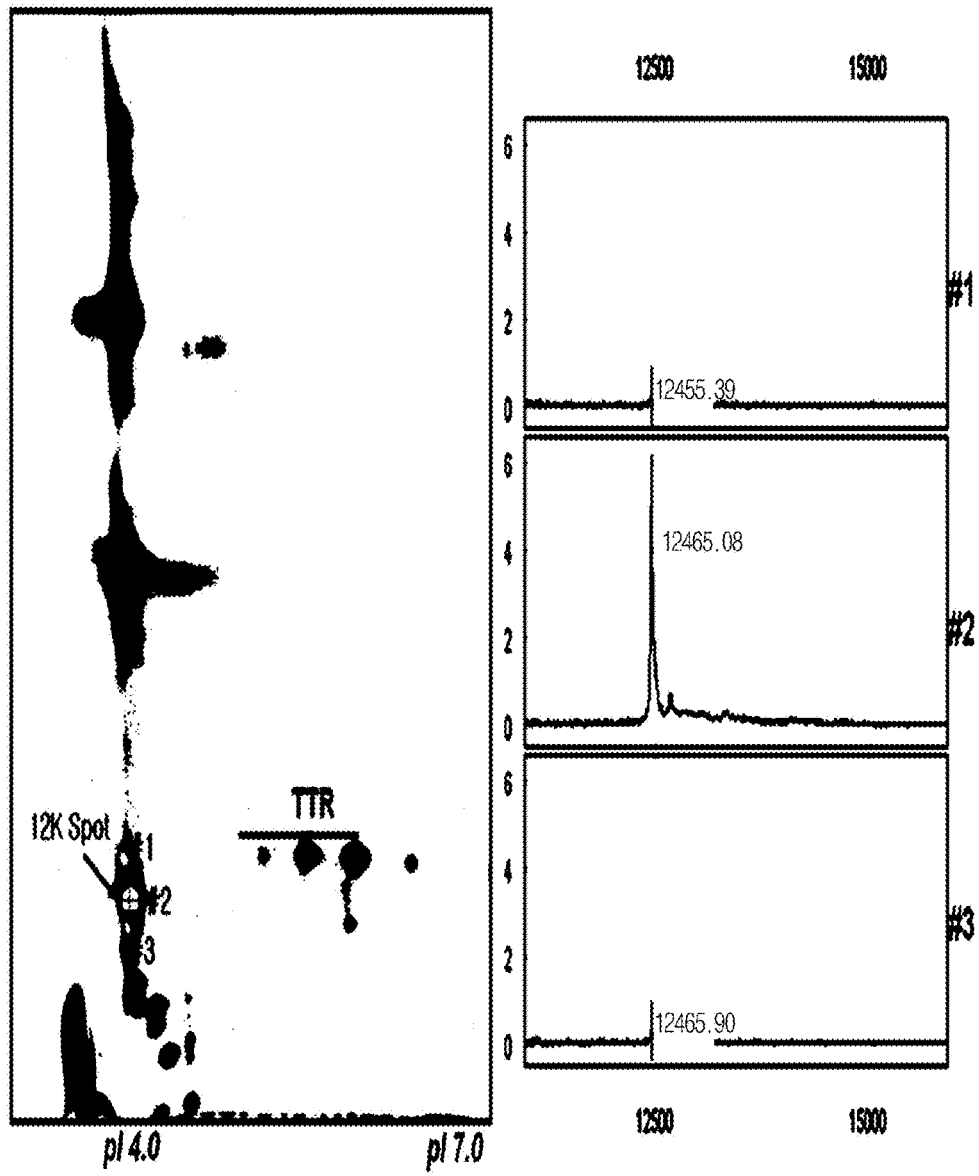
FIG. 8 is a diagram illustrating the result of 2-dimensional electrophoresis of 12.5 kDa peak protein and the result of SELDI-TOF MS performed after eluting the protein.

Upon completion of isoelectric focusing, IPG strip was soaked in equilibration buffer (50 mM Tris-HCl, pH 8.8/6 M Urea/30% glycerol/2% SDS/BPB) for 5 minutes, followed by electrophoresis on 12.5% polyacrylamide gel. Constant current was 10 mA in stage 1 for 30 minutes, and 20 mA in stage 2 for 5 hours. Upon completion of electrophoresis, the gel was stained with Coomassie Blue G-250 (Fluka) for overnight (FIG. 8).

<4-6> Passive Elution

Spots to elute were selected from the gel stained in Example <4-5>, which were cut out with disposable pipetteman tip and washed to remove Coomassie blue dye. Particularly, the washing was performed with 20 μl of 50% ACN/50 mM ammonium bicarbonate three times (5 minutes each). The numbers of washing was determined by the strength of staining. The washed gel spots proceeded to dehydration with 100% ACN for 20 minutes. 5-10 μl of elution buffer (10% formic acid (Fluka), 30% ACN, 20% isopropanol, 40% D.W) was added to the dehydrated gel spot, followed by vigorous shaking for 2 hours at room temperature. 2 μl of eluted protein was placed on NP20 chip, followed by confirmation with SELDI-TOF MS (FIG. 8).

EXAMPLE 5

Identification of 12,451 m/z Protein

<5-1> ESI-Q-TOF MS

The 12451 (m/z) protein spot confirmed by electrophoresis and passive elution in Example 4 was analyzed with ESI-Q-TOF MS/MS (requested to Intuzen Co.) (FIG. 9).

First, in-gel-digestion was performed (Jensen, O. N., et al., *Anal Chem.*, 69, 1706-1714, 1997). Gel spot was loaded in 100 μl of destain solution (50% Methanol in 10% Acetic acid), followed by shaking for 5 minutes. The solution was eliminated and the gel spot was stayed in 200 mM ammonium bicarbonate solution for 20 minutes. The gel spot was dehydrated with 100 μl of acetonitrile and dried with speed vac. The dried gel spot was rehydrated with 20 μl of 50 mM ammonium bicarbonate containing 0.2 g of modified trypsin (Promega) on ice. The remaining solution was eliminated and 30 μl of 50 mM ammonium bicarbonate was added thereto, followed by reaction at 37 for overnight. The peptide solution was desalted and concentrated using C18 nano column constructed by the inventors before mass-analysis. The column was prepared by filling GELoader tip (Eppendorf, Hamburg, Germany) with 100-300 nL of porous reversed R2 material (20-30 um bead size, PerSeptive Biosystems), and air pressure was softly given using 10 and syringe to let the solution go through the column. 30 !i of the peptide mixture was mixed with 30 μl of 5% formic acid, which was loaded on the column. The column was washed with 30 μl of 5% formic acid, followed by elution using 50% methanol/49% $H_2O$/1% formic acid.

The peptide prepared by in-gel digestion proceeded to nano-ESI MS/MS using Q-TOF2 mass-spectrometer (Micromass, Manchester, UK). The source temperature was 80 and 0-5 psi nitrogen pressure was maintained to keep flow rate (10-30 nL/min) stable. 1 kV of electric potential was applied to precoated borocilicate nanoelectrospray needle (EconoTip™, New Objective, USA). To confirm precursor ions using collision-induced dissociation (CID) having comparative collision energy, MS/MS spectrum was recorded. Voltage of cone was 40V. To select precursor ion for fragmentation of hexapole collision cell, quadrupole analyzer was used and argon with the pressure of $6-7 \times 10^{-5}$ mbar was used as collision gas. At that time, collision energy was 20-30V. Product ions were analyzed with orthogonal TOF analyzer equipped with reflector, micro-channel plate detector and a time-to-digital converter. Data was processed by Mass Lynx Windows NT PC system.

At last, protein identification and sequence processing were performed. Amino acid sequences presumably obtained by tryptic peptide MS/MS spectrum and PepSeq, the peptide de-novo sequencing program, were screened through NCBInr and EST databases using MASCOT screening program (www.mnatrixscience.com) and BLAST.

<5-2> N-terminal Sequencing

Upon completion of 2-dimensional electrophoresis In Example <4-5>, the target gel spot for transfer was cut off and transferred on PVDF membrane with 250 V for one hour (using Mini Trans-Blot Cell (Bio-Rad, Hercules, Calif.)). Upon completion of the transfer, the membrane was stained with Coomassie G-250 for overnight. The stained membrane was destained for 10 minutes to eliminate background (10% methanol, 7% acetic acid). N-terminal sequencing was performed by using Procise 492 cLC protein sequencer (Applied Biosystems, USA) at Korea Basic Science Institute.

As a result, the amino acid residue sequence was identified, which was Ser-Glu-Gly-Ser-Ser-Val-Asn (SEQ. ID. NO: 4). This sequence corresponded to the amino acid residue 199-205 of prothrombin precursor (P00734), precisely that is N-terminal region of prothrombin activation peptide fragment 2 (FIG. 10). From the results of ESI-Q-TOF analysis and N-terminal sequencing, the total amino acid sequence of 12451 (m/z) peak could be presumed (Ser 199-Gly 313). This fragment was identified as des-R F2 which was prothrombin activation peptide fragment 2 lacking of C-terminal arginine. And the molecular weight theoretically calculated (12,457 Da) was consistent with the peak found in SELDI-TOF MS (12,451 m/z) (see FIG. 11).

INDUSTRIAL APPLICABILITY

As explained hereinbefore, the diagnostic kit and method of the present invention facilitate diagnosis, screening and evaluation of disease progress of liver cancer, breast cancer and stomach cancer, so that they can contribute to quick response to disease to increase survival rate of cancer patients and they can contribute to reduce national economic loss caused by dealing with cancer.

SEQUENCE LIST TEXT

SEQ. ID. NO: 1 is the amino acid sequence of des-R prothrombin activation peptide fragment F2 (des-R F2) originated from human serum.

SEQ. ID. NO: 2 is the amino acid sequence of an epitope located at N-terminal region of des-R prothrombin activation peptide fragment F2.

SEQ. ID. NO: 3 is the amino acid sequence of an epitope located at C-terminal region of des-R prothrombin activation peptide fragment F2.

SEQ. ID. NO: 4 is the amino acid sequence of N-terminal region of des-R-prothrombin activation peptide fragment F2, which corresponds to the amino acid residues 199-205 of prothrombin precursor (P00734).

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A method of diagnosing cancer in a subject in need thereof, comprising:
   1) measuring expression of des-R-prothrombin activation peptide fragment F2 in samples selected from the group consisting of blood, serum and plasma, which are respectively obtained from a test subject and a normal subject, wherein the measuring is conducted by a method selected from the group consisting of:
      2-dimensional gel electrophoresis;
      ESI-Q-TOF MS (Electrospray Ionisation Quadrupole-Time-of-Flight Mass Spectrometry);
      MALDI-TOF MS (Matrix-Assisted Laser Desorption and Ionization Time-of-Flight Mass Spectrometry);
      SELDI-TOF MS (Surface-Enhanced Laser Desorption and Ionization Time-of-Flight Mass Spectrometry);
      a kit or biochip containing antibodies specifically binding to des-R prothrombin activation peptide fragment F2;
   2) comparing the measured expression level of des-R-prothrombin activation peptide fragment F2 in the sample of the test subject with that of the normal subject, and selecting a test subject demonstrating reduced des-R-F2 expression; and
   3) determining that the test subject selected at step 2) has a cancer.

2. The method of claim 1, wherein the selection of step 2) is performed by bioinformatics techniques.

3. The method of claim 1, wherein the cancer is selected from the group consisting of liver cancer, breast cancer and stomach cancer.

4. The method of claim 1, wherein the des-R prothrombin activation peptide fragment F2 characteristically has the amino acid sequence represented by SEQ ID NO: 1.

5. The method of claim 1, wherein the des-R-prothrombin activation peptide fragment F2 is down-regulated in a subject with cancer, compared with in a normal subject.

6. The method of claim 1, wherein the des-R-prothrombin activation peptide fragment F2 contains an epitope having the amino acid sequence represented by SEQ ID NO: 2 at N-teminal region and another epitope having the amino acid sequence represented by SEQ ID NO: 3 at C-terminal region.

7. The method of claim 1, wherein the antibodies are specifically bound to a solid substrate.

8. The method of claim 1, wherein the antibodies are a conjugate labeled with a ligand, a coloring enzyme, a fluorescent material, a radioisotope or a colloid, 9. The method of claim 8, wherein the antibodies are quantified by i) SPR (surface plasmon resonance) or SPRI (surface plasmon resonance imaging) or ii) measuring fluorescence from the fluorescent marker attached to the antibody for detection.

10. The method of claim 1, wherein the kit or the biochip additionally includes antibody specific binding proteins.

11. The method of claim 10, wherein the antibody specific binding proteins are secondary antibodies specifically binding to protein A or the antibody for detection.

12. The method of claim 10, wherein the antibody specific binding proteins are labeled with a coloring enzyme, a fluorescent material, a radioisotope or a colloid.

13. The method of claim 10, wherein the antibody specific binding proteins are quantified by i) SPR (surface plasmon resonance) or SPRI (surface plasmon resonance imaging) or ii) measuring fluorescence from the fluorescent marker attached to the protein.

14. The method of claim 1, wherein the measuring is conducted by 2-dimensional gel electrophoresis.

\* \* \* \* \*

UNITED STATES PATENT AND TRADEMARK OFFICE
CERTIFICATE OF CORRECTION

PATENT NO.      : 8,435,748 B2                                              Page 1 of 1
APPLICATION NO. : 12/993198
DATED           : May 7, 2013
INVENTOR(S)     : Kim et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 267 days.

Signed and Sealed this
Eighth Day of September, 2015

Michelle K. Lee
*Director of the United States Patent and Trademark Office*

SEQUENCE LISTING

```
<160> NUMBER OF SEQ ID NOS: 4

<210> SEQ ID NO 1
<211> LENGTH: 112
<212> TYPE: PRT
<213> ORGANISM: Homo sapiens

<400> SEQUENCE: 1

Ser Glu Gly Ser Ser Val Asn Leu Ser Pro Pro Leu Glu Gln Cys Val
1               5                   10                  15

Pro Asp Arg Gly Gln Gln Tyr Gln Gly Arg Leu Ala Val Thr Thr His
            20                  25                  30
```

```
Gly Leu Pro Cys Leu Ala Trp Ala Ser Ala Gln Ala Lys Ala Leu Ser
        35                  40                  45
Lys His Gln Asp Phe Asn Ser Ala Val Gln Leu Val Glu Asn Phe Cys
        50                  55                  60
Arg Asn Pro Asp Gly Asp Glu Glu Gly Val Trp Cys Tyr Val Ala Gly
 65                  70                  75                  80
Lys Pro Gly Asp Phe Gly Tyr Cys Asp Leu Asn Tyr Cys Glu Glu Ala
                 85                  90                  95
Val Glu Glu Glu Thr Gly Asp Gly Leu Asp Glu Asp Ser Asp Arg Ala
                100                 105                 110

<210> SEQ ID NO 2
<211> LENGTH: 12
<212> TYPE: PRT
<213> ORGANISM: Homo sapiens

<400> SEQUENCE: 2

Ser Glu Gly Ser Ser Val Asn Leu Ser Pro Pro Leu
 1               5                   10

<210> SEQ ID NO 3
<211> LENGTH: 12
<212> TYPE: PRT
<213> ORGANISM: Homo sapiens

<400> SEQUENCE: 3

Gly Leu Asp Glu Asp Ser Asp Arg Ala Ile Glu Gly
 1               5                   10

<210> SEQ ID NO 4
<211> LENGTH: 7
<212> TYPE: PRT
<213> ORGANISM: Homo sapiens

<400> SEQUENCE: 4

Ser Glu Gly Ser Ser Val Asn
 1               5
```